United States Patent [19]

Minshall et al.

[11] Patent Number: 5,496,302
[45] Date of Patent: Mar. 5, 1996

[54] METHOD FOR STERILIZING

[75] Inventors: Billy W. Minshall, Mission Viejo, Calif.; John E. Nygard, Skokie, Ill.; Kwame Sintim-Damoa, Vernon Hills, Ill.; Richard Giesler, Deerfield, Ill.; Archie Woodworth, Barrington, Ill.; Kailash Purohit, Winnetka, Ill.

[73] Assignee: Baxter International Inc., Deerfield, Ill.

[21] Appl. No.: 876,125

[22] Filed: Apr. 29, 1992

Related U.S. Application Data

[60] Continuation of Ser. No. 678,811, Apr. 1, 1991, abandoned, which is a division of Ser. No. 321,698, Mar. 10, 1989, Pat. No. 5,009,654.

[51] Int. Cl.⁶ ................................................. A61B 19/00
[52] U.S. Cl. ............................................ 604/410; 604/408
[58] Field of Search ................................. 604/410, 408

[56] References Cited

U.S. PATENT DOCUMENTS

| | | | |
|---|---|---|---|
| 3,968,195 | 7/1976 | Bishop | 604/410 |
| 4,157,723 | 6/1979 | Granzow et al. | 604/905 X |
| 4,223,675 | 9/1980 | Williams | 604/410 |
| 4,332,122 | 6/1982 | Williams | 604/408 X |
| 4,340,049 | 7/1982 | Munsch | 604/408 X |
| 4,410,026 | 10/1983 | Buggs et al. | 604/408 X |
| 4,610,670 | 9/1986 | Spencer | 604/905 X |
| 4,652,763 | 3/1987 | Nablo | 250/492.3 |
| 4,828,557 | 5/1989 | Persidsky | 604/408 |

OTHER PUBLICATIONS

Vroom, "Electron–Beam Sterilization, An Alternative To Gamma Irradiation," *Medical Device & Diagnostic Industry*, Nov. 1980.

*Primary Examiner*—Robert A. Hafer
*Assistant Examiner*—Brian E. Hanlon
*Attorney, Agent, or Firm*—Bradford R. L. Price; Joseph B. Barrett; Andrew G. Kolomayets

[57] ABSTRACT

Methods are disclosed for sterilizing a selected portion of a product and for assembling a sterile product from two or more parts which can not be sterilized with the same form of sterilization. A sterile product produced by these methods is also disclosed. The method for sterilizing may include sterilizing a selected portion of the product by exposing the selected portion to an electron beam, while shielding the remainder of the product from the radiation of the electron beam. The method of assembling a sterile product from two or more component parts may include the steps of sterilizing the first part of the product, isolating a portion of the first part from the remainder of the first part, attaching the second part to the isolated portion of the first part, and exposing the isolated portion to a form of sterilization which is deleterious to the remainder of the first part, while shielding the remainder of the first part from such form of sterilization.

6 Claims, 6 Drawing Sheets

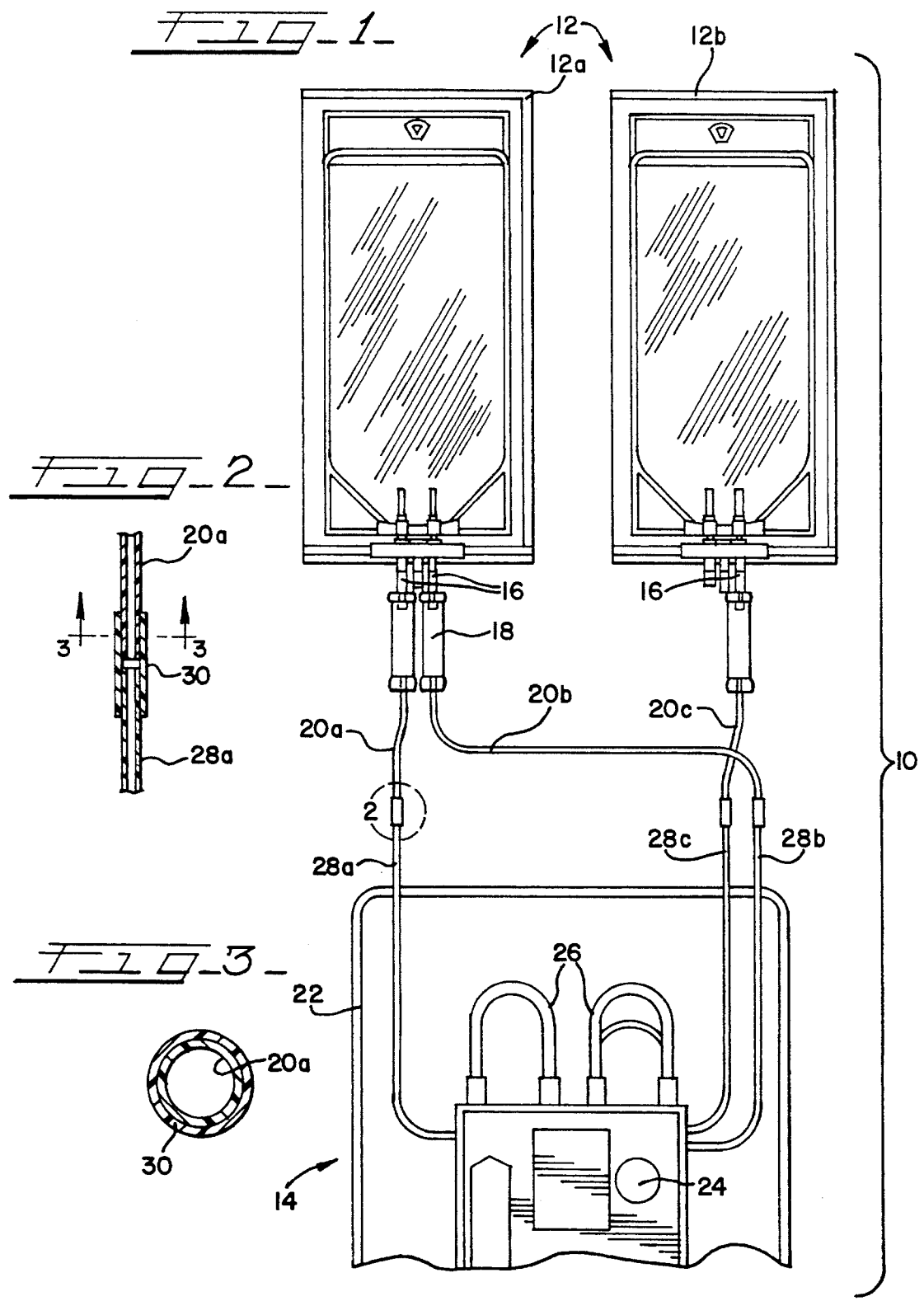

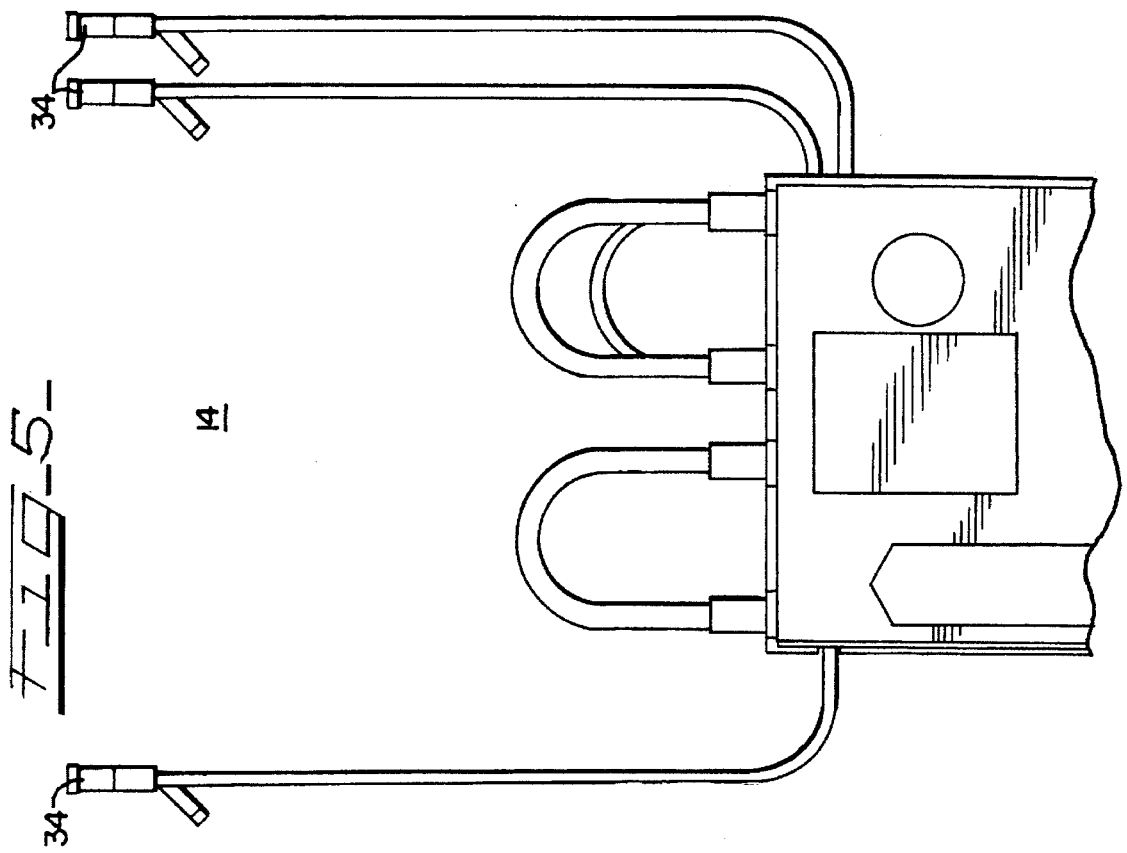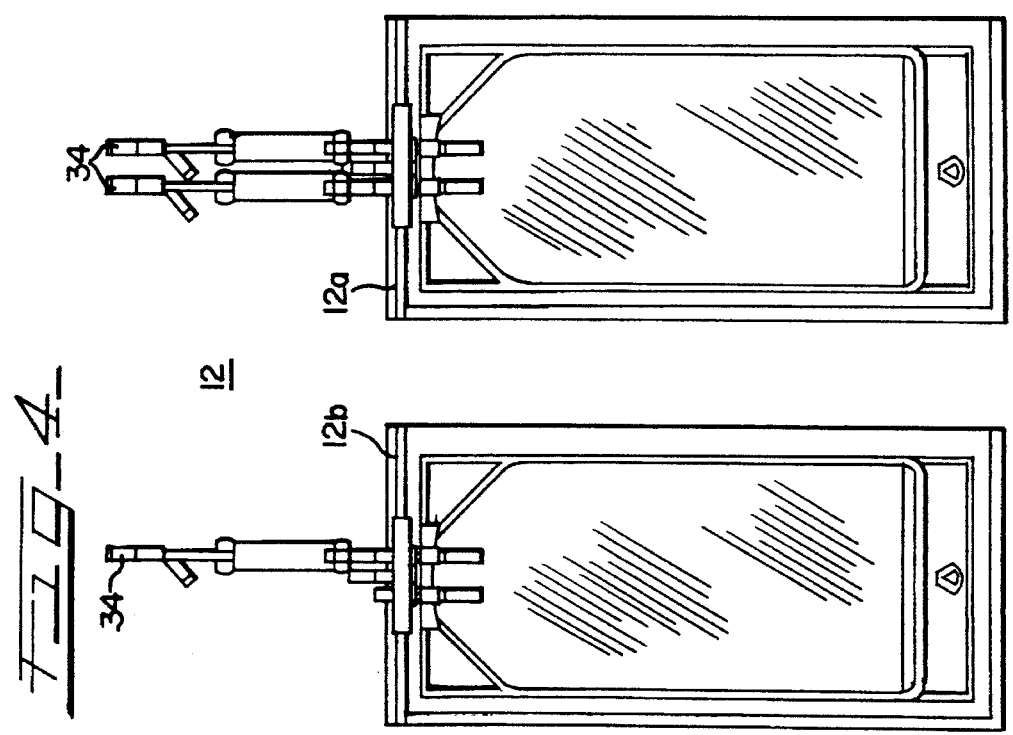

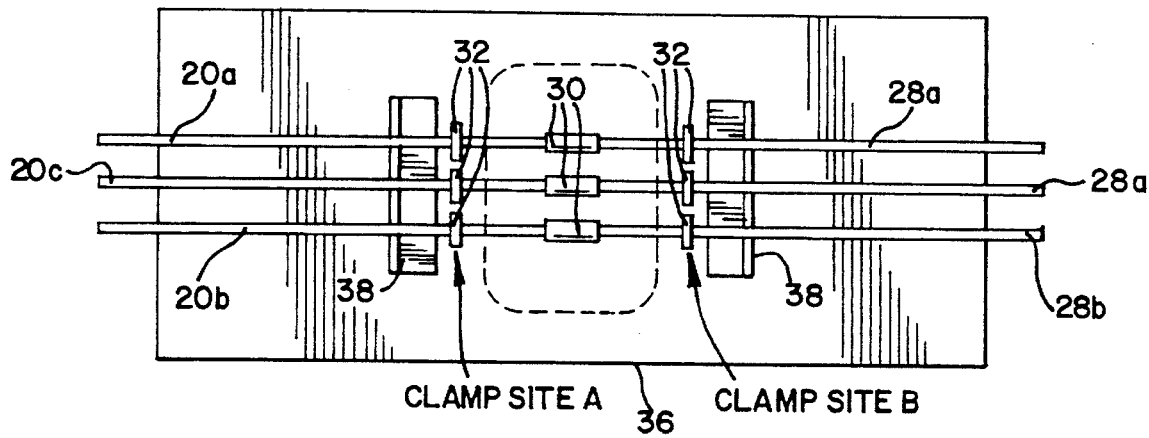
FIG-6-
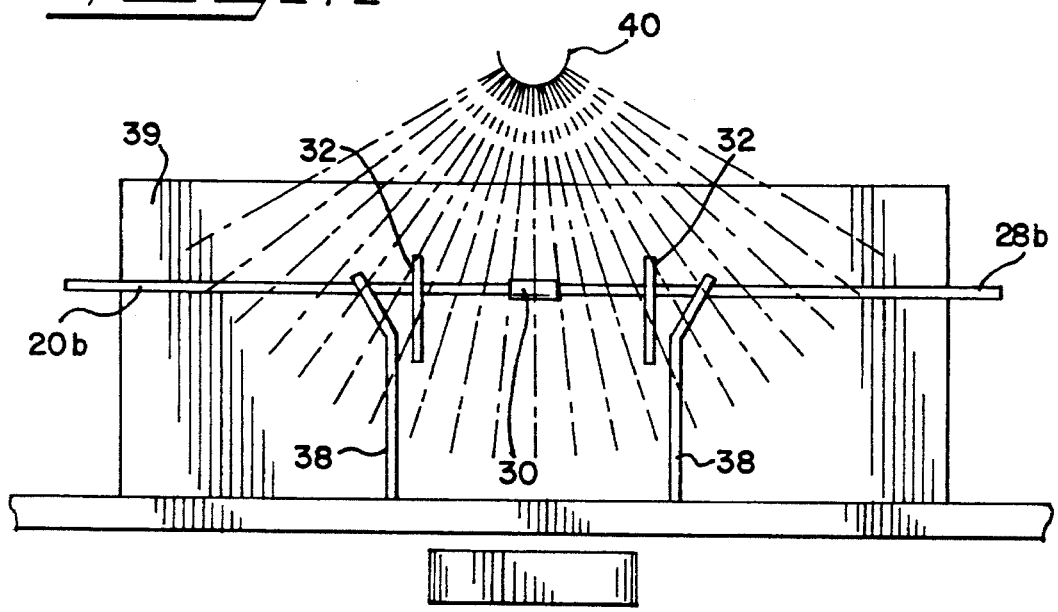
FIG-7-

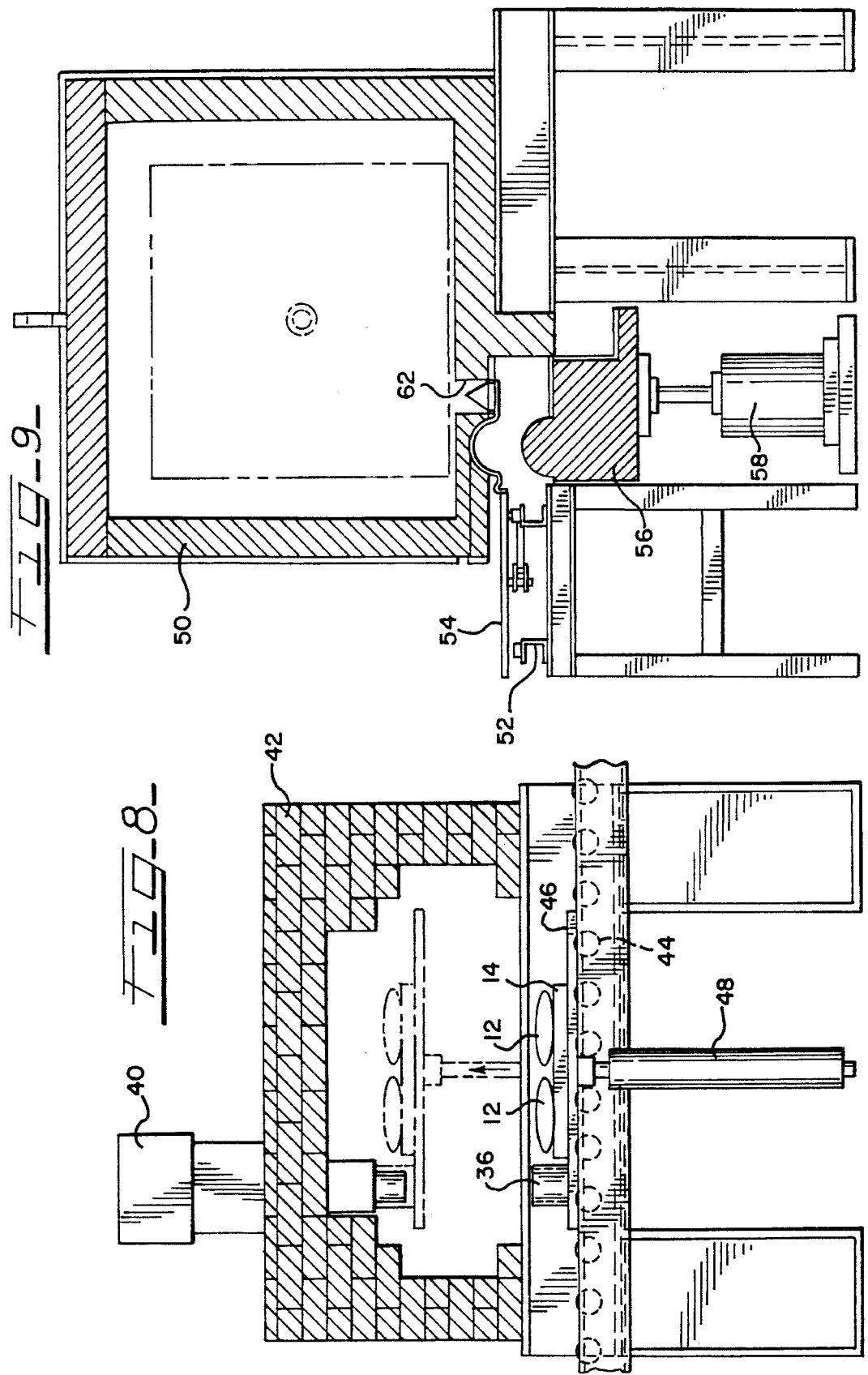

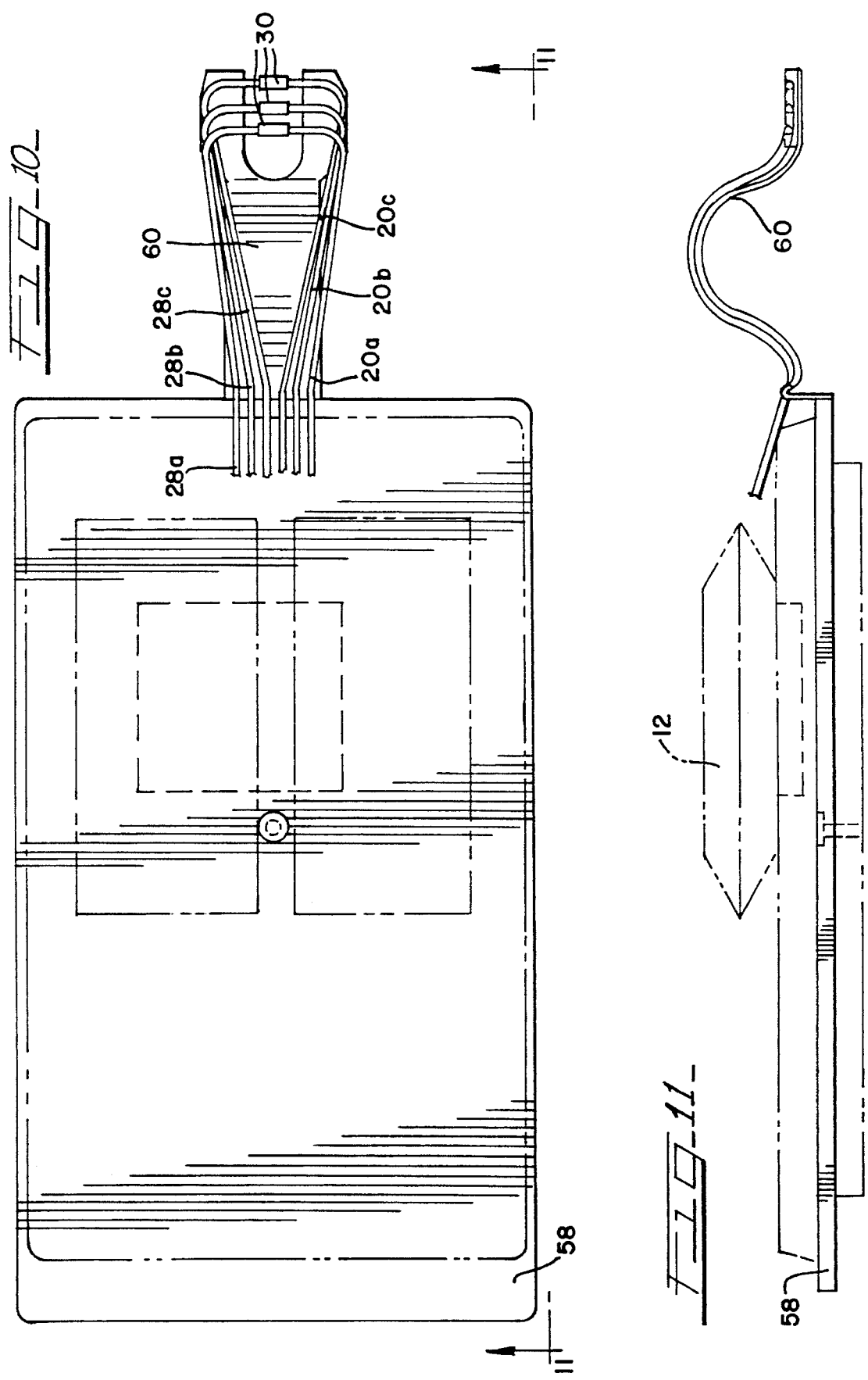

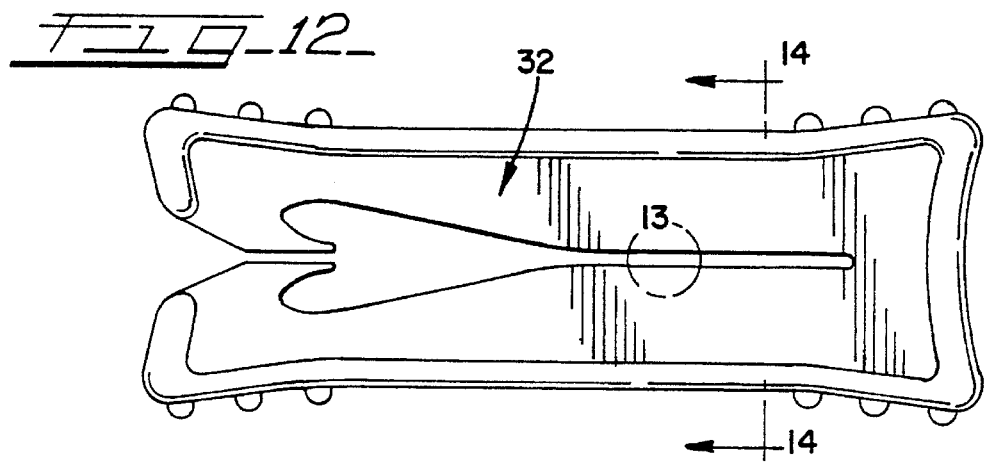
FIG_12_
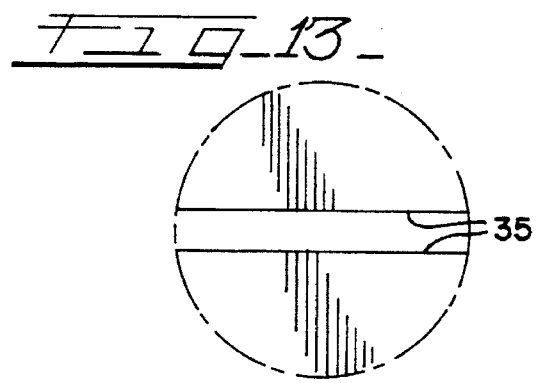
FIG_13_
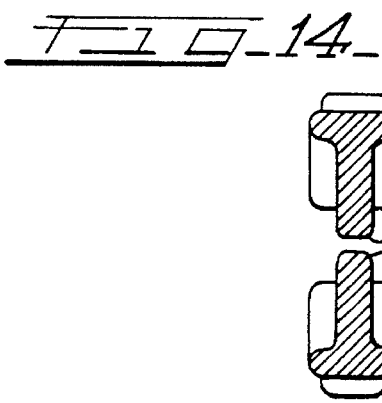
FIG_14_
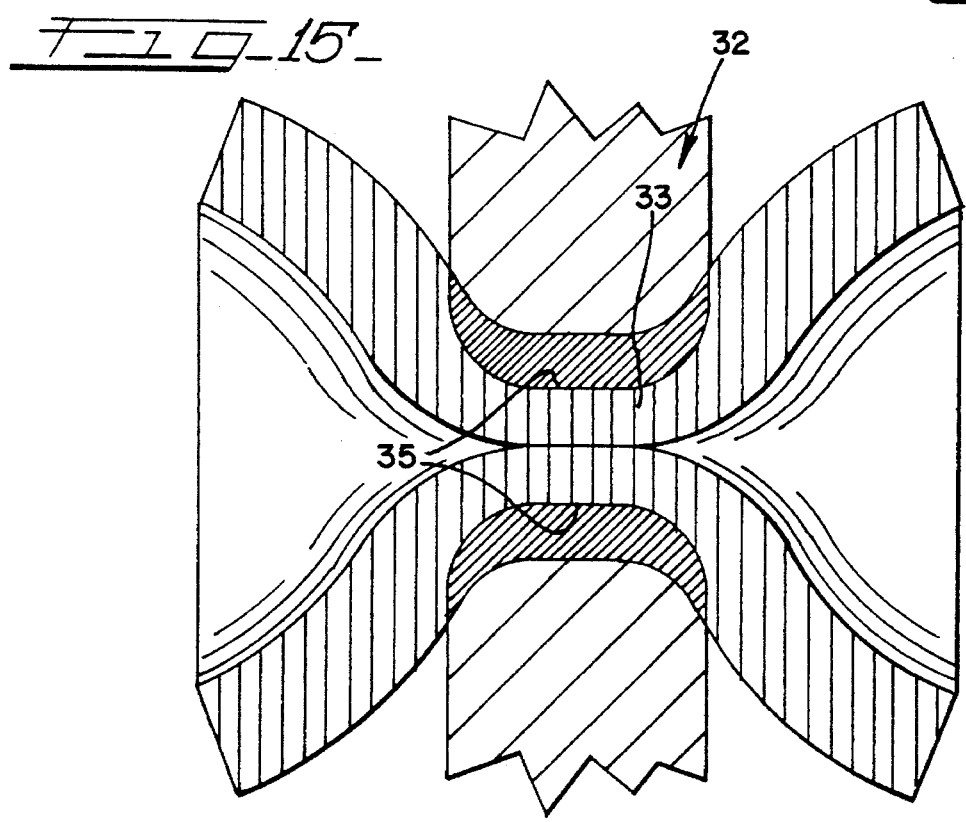
FIG_15_

METHOD FOR STERILIZING

This is a continuation of application Ser. No. 07/678,811 filed Apr. 1, 1991, which is a division of U.S. Ser. No. 07/321,698 filed on Mar. 10, 1989, now U.S. Pat. No. 5,009,654.

BACKGROUND OF THE INVENTION

The present invention relates generally to sterile products and to methods for sterilizing and assembling such products. More particularly, the present invention relates to sterile products and to methods for sterilizing and assembling such products, wherein the products have two or more portions which are mutually incompatible with regard to the method of sterilization.

Pre-sterilized, disposable medical products are commonplace in the United States and other countries throughout the world. One heretofore significant restraint on the design, development, and manufacture of such products has been the fact that certain desirable products would include portions or components which are mutually incompatible from a sterilization standpoint. For example, it may be desirable to provide a unitary, pre-sterilized product which has a sealed liquid or powder drug component and a plastic apparatus component, such as a tubing or flow control set, for dispensing the drug.

The integral product, however, cannot be sterilized after assembly because not all of the components may be subjected to the same form of sterilization. For example, the plastic apparatus component (e.g. the tubing or flow control device) may only be sterilizable with radiation or gas. The drug component, on the other hand, may not be sterilizable with either gas or radiation—gas sterilization would be ineffective to sterilize a sealed drug, while exposing the drug to radiation may lead to product degradation or otherwise have a deleterious effect on the drug.

Accordingly, efforts have been made to devise means for joining, in a sterile manner, components which are individually pre-sterilized. One example of such a product is the blood processing (apheresis) kit manufactured and sold by the Fenwal division of Baxter Healthcare Corporation of Deerfield, Ill. Typically, the blood processing kit (such as those produced by Baxter Healthcare) consists of two or more containers filled with medical solutions, connecting tubes, and a flow control subassembly. The solution containers may be filled with anticoagulant to prevent blood clotting, dextrose as an energy source for blood cells, saline, or other medical liquid utilized in the treatment of the patient or in the collection of blood components. A network of tubing connects the solution containers and the flow control subassembly.

The current process for manufacturing such apheresis kits involves a multi-step process of assembling an entire apheresis kit with empty solution containers; filling separate containers with the desired solution; separately sterilizing the assembled kit (with the empty containers) and the filled containers; transferring in a sterile manner the pre-sterilized solution into the pre-sterilized empty solution containers; and discarding the original (now empty) solution containers.

The sterile transfer of solution is achieved through the use of a sterile docking device such as the device disclosed in U.S. Pat. No. 4,157,723. The sterile docking device shown there utilizes a pair of mating halves, with facing membranes. One half of the docking device is connected to the empty pre-sterilized containers, and the other half is connected to the full pre-sterilized container. After the halves are joined, the docking device is exposed to radiant energy, causing the membranes within the docking devices to melt and form a sterile fluid pathway through the device. Once this pathway is formed, the previously sterilized solution is manually transferred from the original bag to the empty bag attached to the kit. After transfer, the transfer tubing is sealed and cut, and the emptied bags and the docking devices are discarded.

While this process has generally worked satisfactorily, it entails the step of transferring solution from one container to another in a sterile manner and all the extra quality control procedures associated with such a step. Also, once the solution is transferred, the original solution bags and sterile docking devices cannot be reused and must be discarded, adding cost to the final product.

For these reasons, it is a general object of the present invention to provide an improved sterile product of the type described above and improved methods for sterilizing and assembling such products.

This and other objects of the present invention are set forth in the following detailed description of the illustrated embodiment of the present invention.

SUMMARY OF THE INVENTION

The present invention is directed generally to sterile integral products, to methods for assembling such products, and to methods for sterilizing a selected portion of such products. The sterile integral product may consist of a first portion which is unsuited to selected forms of sterilization, such as radiation, and a second portion which is particularly well suited to utilizing such selected forms of sterilization. In accordance with one aspect of the present invention, the second portion of the product may be exposed to the selected form of sterilization, while the other portion of the product is shielded from the selected form of sterilization. This may be performed with the two portions integrally connected and in relatively close association with each other.

In another embodiment of the present invention the first portion may be sterilized prior to joinder with the second portion, in a manner which achieves a sufficient degree of sterilization while not adversely affecting it, such as steam heat. The second portion may be sterilized prior or subsequent to joinder with the first portion, utilizing a form of sterilization such as gas or radiation, which is unsuitable for sterilizing the first portion. The portions are joined by first isolating a part of the first portion and attaching it to the second portion. If the second portion is also sterilized prior to joinder, then a part of the second portion is also isolated. The isolated parts of the first and second portions are then joined and the joined isolated portions, or the isolated part of the first portion and all or some of the second portion if the second portion is not pre-sterilized, are then sterilized in one of the selected manners, while the remainder of the first portion is shielded from adverse effect by such selected form of radiation.

The isolated parts of the first and second product portions may include means defining a fluid flow conduit between the first and second product portions. The fluid flow conduits may be isolated from the remainder of the product portions by mechanical means such as clamps, valves or the like, or by the inherent characteristics of the conduit itself, which limits possible ingress or movement of bacteria or organisms toward the remainder of the product portion. In any event, the isolated portions are subjected to one of the selected forms of sterilization so as to assure sterility of the isolated portions, while the remainder of the first product portion is shielded to prevent adverse effects. The isolating means may then be removed, if necessary, to yield a connected integral sterile product, made up of portions which are otherwise mutually incompatible from a sterilization standpoint.

In accordance with a further aspect of the present invention, the preferred selected form of sterilization is irradiation by electron beam. An electron beam may be easily focused on the isolated portions, readily started and stopped. An electron beam may also be readily shielded from any personnel involved in product manufacture and/or from the remainder of the product which should not be exposed to radiation.

The present invention has particular application in the assembly and sterilization of medical products containing medical liquids or drugs. For example, in one version of the present invention, the first product portion includes one or more sealed containers filled with a medical liquid or drug which is adversely affected by ethylene oxide gas and/or radiation sterilization. The second product portion may comprise an administration apparatus which is to be directly attached to the first portion for administering the liquid or drug to a patient. Such administration apparatus, however, is only sterilizable in a manner which is incompatible with the fluid or drug, such as radiation or ethylene oxide gas.

In accordance with the present invention, the first portion is separately sterilized by autoclaving, i.e., steam heating, the container and contents, while the second portion may be separately sterilized by either gas or radiation. Once the product portions have been separately sterilized, the product is assembled.

In one arrangement, each portion of the product includes means defining a flow path, e.g., plastic tubing, in communication with its respective product portion. In accordance with the present invention, the entire product is assembled by isolating at least a portion of the flow paths from the remainder of the product portions and joining the isolated sections of the flow path together. The flow path may be isolated by clamping the flow paths associated with the first and second product portions or, alternatively, by providing a normally-closed frangible connector in the flow path of each portion. If the flow paths have a sufficiently small bore, there may also be isolation by the inherent resistance to flow within the inside of a tube, thus eliminating the need for separate clamping or blockage of the flow path.

After joinder, the isolated fluid flow path is sterilized by exposing it to an electron beam. During exposure of the flow path to the electro beam, the remainder of the first product portion is shielded from the beam in order to protect the medical fluid or drug within the container from any adverse effects of radiation.

Further features of the present invention will become more fully apparent in the following description of the illustrated embodiments and from the appended claims.

DETAILED DESCRIPTION OF THE DRAWINGS

FIG. 1 is a vertical plan view of a sterile product embodying the present invention and assembled and sterilized in accordance with the method of the present invention.

FIG. 2 is an enlarged cross-sectional view of the connected conduits which form a portion of the product of FIG. 1.

FIG. 3 is a cross-sectional view taken along line 3—3 of FIG. 2.

FIG. 4 is a plan view of two containers of medical liquid or the like which comprise a portion of the product depicted in FIG. 1.

FIG. 5 is a plan view, partially removed, of liquid administration and processing apparatus which forms another portion of the product depicted in FIG. 1.

FIG. 6 is a plan view of a fixture, with portions of the product of FIG. 1 mounted on the fixture in the position for sterilization on isolated portion of the product.

FIG. 7 is a diagrammatic plan view of the fixture and product portions of FIG. 6, depicting the sterilization of the isolated portions by irradiation.

FIG. 8 is a sectional view of apparatus which may be employed in carrying out the sterilization method of the present invention.

FIG. 9 is a sectional view of alternative apparatus for performing the sterilization of the product portions depicted diagrammatically in FIG. 7.

FIG. 10 is a top view of a fixture for use with the apparatus depicted in FIG. 9 for carrying out the present invention.

FIG. 11 is a side view of the fixture of FIG. 10 taken along line 11—11 of FIG. 10, and depicting a medical fluid container in phantom.

FIG. 12 is a plan view of a slide clamp which may be used in the practice of the present invention.

FIG. 13 is an enlarged plan view of the gripping area of the clamp of FIG. 12 taken at the area designated 13 in FIG. 12.

FIG. 14 is a cross-sectional view of the clamp of FIG. 12, taken along line 14—14.

FIG. 15 is a partial cross-sectional view of the clamp of FIG. 12, depicting the sealing action when applied to flexible plastic tubing.

The present invention is generally embodied in a product 10, and in the methods of sterilizing and assembling such product, which product includes one or more medical liquid containers 12 and liquid administration or processing apparatus 14. In accordance with the present invention, one product portion, the containers of medical liquid may not be radiation sterilized because of deleterious product effects, and may not be gas sterilized because they are sealed containers. As a result, the most effective sterilization for such medical liquids is autoclaving. The other product portion 14 comprises apparatus for administering or processing the liquid contained in the containers 12. That product portion, however, is not effectively sterilized by autoclaving, but must be radiation sterilized or sterilized using ethylene oxide gas.

The product, in FIG. 1, which is depicted for purposes of illustration only and not for limitation, is a closed apheresis kit or circuit, which may be used, for example, with the CS-3000 Blood Cell Separator marketed by Baxter Healthcare Corporation of Deerfield, Ill. A typical apheresis set is shown in more detail, for example, in U.S. Pat. No. 4,410,026 to Boggs. In this particular product, container 12a is a flexible plastic bag containing a medical fluid, such as a parenteral solution or, more particularly, a 0.9 percent sodium chloride solution for use in the apheresis process. Container 12b is also preferably a flexible plastic bag. It may contain, for example, a blood preservative, such as anticoagulant citrate dextrose.

The bags of liquid are attached to the liquid administration or processing apparatus 14 through outlet ports 16 disposed at the end of the bag and in communication between the interior of the bag and drip chambers 18, which may be used for monitoring the flow rate of solution from the bags. Flexible plastic tubing segments 20a, b and c, respectively, extend from the bottoms of the drip chambers for attachment to the liquid administration and processing apparatus 14.

The liquid administration and processing apparatus 14 comprises a rigid, plastic panel 22 which mounts flow control valves such as 24 and looped tubing portions 26 for cooperation with rotary peristaltic pumps, which are provided on the CS-3000 Blood Cell Separator manufactured and sold by Baxter Healthcare Corporation. The housing 22 also mounts the fluid circuitry for controlling the flow of liquid in the overall system in cooperation with the CS-3000 Blood Cell Separator. The details of this housing and fluid circuitry system are depicted in more detail in issued public patents, such as U.S. Pat. No. 4,410,026, referred to above. To that extent, the '026 patent is incorporated by reference herein.

The tubing segments 20a, b, and c which extend from the drip chambers of the medical liquid containers are joined to mating tubing segments 28a, b and c of the liquid administration or processing apparatus 14 in the manner depicted more clearly in FIGS. 2 and 3. As shown in FIG. 2, tubings 20a and 28a are joined in fluid communication by a surmounting flexible plastic sleeve 30. The end of each tubing segment 20a and 28a is inserted into the end of the flexible plastic sleeve 30 and sealed, such as by heat, sonic or solvent bonding therewithin. Solvent bonding, with a solvent such as with cyclohexanone, is simple and is presently the preferred method for joining the tubing segments in a sealed manner.

FIG. 3 depicts the joint of FIG. 2 in cross-section, taken along line 3—3 of FIG. 2. It shows the tubing segment 20a contained within and sealed to the interior surface of the flexible sleeve 30. This drawing will be referred to later in discussing the sterilization that takes place in accordance with the method of the present invention.

FIGS. 4 and 5 depict the medical liquid containers 12 and the liquid administration or processing apparatus 14, respectively, as they appear prior to joinder. More particularly, FIG. 4 depicts the containers 12a and 12b as they would appear at the time of their sterilization. As described briefly earlier, because containers 12a and 12b are sealed, gas sterilization, such as the use of ethylene oxide, may be unavailable, depending on whether the bag is gas permeable, for sterilizing these products. Moreover, radiation sterilization is not preferred because of possible deleterious effects on the product contents which results from the radiation. Accordingly, the containers 12a and 12b are preferably autoclaved, via steam heat, to achieve or exceed the appropriate sterility level required by the United States Food and Drug Administration.

In contrast to the liquid containers 12, the liquid administration and processing apparatus 14 is preferably sterilized with radiation or gas. Because of the complex tubing circuitry and the nature of the materials and construction of the liquid administration and processing apparatus, autoclaving is not a preferred sterilization technique for the apparatus 14. Accordingly, the liquid containers 12 and the liquid administration and processing apparatus 14 are preferably sterilized separately, by the particular method of sterilization which is best suited for that product portion.

In accordance with the present invention, these product portions, i.e., the liquid containers 12 and the liquid administration and processing apparatus 14, are preferably joined in a manner which does not require resterilization or sterilization of the entire combined product. Such, of course, would be impractical because the product portions, that is the medical liquid containers 12 and the liquid administration and processing apparatus 14, are mutually incompatible insofar as the sterilization method is concerned.

As diagrammatically illustrated in FIGS. 6 and 7, the product portions are joined by first isolating a terminal end portion of the tubing segments 20a–c and 28a–c from the remainder of the particular product portion. For example, the terminal end of tubing 20a is isolated from the remainder of the tubing and the associated drip chamber. "Isolation" means blockage of the tubings from ingress by bacteria or other airborne microorganisms. In the preferred embodiment, the terminal end portions of the tubings 20a and 28a are isolated from the remainder of the tubing and the product portions by removable plastic, radiation permeable slide clamps 32. Alternatively, the end portions may be isolated by internal frangible closures, such as those depicted in U.S. Pat. Nos. 4,181,140 and 4,294,247. Such frangible closures would normally seal the tubing, and would be open only after joinder and sterilization of the joined, isolated regions were complete. Regardless of whether slide clamp, internal frangible closures or other means are used for isolating the terminal end portions of the tubing, preferably the material used for such clamps or closures would be as nearly radiation transparent as possible to assure that the terminal end portions, in their entirety, including any portions contained within the clamps themselves, would be sterilizable by radiation in general, and electron beam radiation in particular.

The presently preferred slide clamp 32 is depicted in more detail in FIGS. 12 through 14. The depicted slide clamp has previously been sold by the Fenwal Division of Baxter Healthcare Corporation, under product code no. 4R4423, for use in the collection and laboratory processing of blood and blood components. The slide clamp acts as a flow occlusion device, similar to a hemostat. By placing the clamp on the outside of the tubing, the interior walls of the tubing are compressed, thereby occluding flow while theoretically maintaining sterility of the fluid path beyond the slide clamp (as shown, e.g., in FIG. 15).

In the present application, the slide clamp is utilized for clamping the tubing segments 20a–c and 28a–c, tubing which preferably has an inside diameter of 0.095 +/– 0.003 inches and an outside diameter of 0.146 +/– 0.002 inches. The portion of the slide clamp for clamping the tubing, depicted enlarged in FIG. 13, preferably has a gap opening of 0.026 inches with a tolerance of +0.005 and –0.004 inches).

When tubing with the above-identified dimensions is placed in the clamping or gripping portion of the clamp, the tubing is tightly gripped and sealed with a compressive force which is believed to be approximately 175 pounds per square inch. FIG. 15 depicts the gripping action in more detail, with the area depicted by numeral 33, being a representation of the compressed portion of the tubing wall, being compressed by the clamp jaws 35.

Before describing the actual steps involved in sterilization, however, there is one further alternative for isolating the terminal end portions of the tubing segments. Under normal assembly conditions, particularly those associated with clean room environments, microorganism ingress into open tubing would occur only in the terminal end portion, and the remainder of the tube and the product portion would remain sterile by reason of the static condition of air within the tube and the inherent resistance to flow of microorganisms into the tube through the open terminal end. Thus, under these conditions, a positive barrier may not even be required to prevent contamination of the remainder of the product. However, slide clamps, internal frangible closures and the like have the advantage of providing a positive barrier to ingress of bacteria or microorganisms and are preferred at the present time.

In accordance with the present invention, the end segments of the tubings 20a–c and 28a–c are isolated by slide clamps 32 prior to joinder. The sterile end covers 34 (FIGS. 4 and 5) of each tubing segment are then removed and the ends of the tube are inserted into the flexible plastic sleeve 30 and solvent sealed therewithin. Following that step, the tubing is preferably mounted on a fixture 36, such as that generally shown in FIG. 6. As may be seen there, the tubing is held in place by a pair of tubing retainers 38, with the tubing sleeve 30 and slide clamps 32 positioned between the retainers.

The fixture 36, with the tubing segments positioned thereon, is then exposed to a radiation source 40, as is figuratively shown in FIG. 7. The radiation source 40 is preferably an electron beam. During the radiation of the isolated tubing end portions, the remainder of the products, and in particular the medical liquid containers 12 are shielded from the radiation effects of the electron beam by an aluminum wall 39 or the like, while they remain connected to the liquid administration and processing apparatus 14.

Electron beam radiation is particularly advantageous in this application. Electron beams are unidirectional and may be relatively narrowly focused. Also they may be readily turned on and off—unlike gamma radiation sources, which of course decay continuously whether or not actually being used for product sterilization. Further, radiation from the electron beam may be readily shielded from other portions of the product and from personnel involved in connection with the manufacture of the product.

An accelerator such as a linear accelerator is used to generate the electron beam. Various studies have been completed to determine the appropriate power and radiation requirements to achieve sterilization, particularly at the juncture of the tubing segments and sleeve 30, where there is a double wall thickness, as shown in FIG. 3.

Initial studies were conducted using a 0.6 MeV pulsed power electron beam instrument manufactured by Pulse Sciences, Inc. Connection tubings were fabricated from radiation grade polyvinylchloride plastic of size typical for medical fluid administration apparatus, such as set forth above. Far West Technology (FWT) dosimeters (FWT-60-00, batch 6FM) and a FWT Radiachromic Reader were used to quantify radiation dose.

Radiation-resistant spores of *Bacillus pumilus* were utilized as a biological indicator. The D-value of this organism is 0.15 Mrad as determined by Cobalt 60 irradiation of paper strips. The spore suspensions were prepared by North American Science Associates, Inc., Northwood, Ohio. For the dosing studies, intact, previously sterilized tubings were placed in an isolation fixture and clamped. Ten microliters (approximately $10^6$ spores) of the suspension of test organisms were placed in the interior of the tubing at a fixed site. Each tubing was then cut at that site and subsequently rejoined using a larger diameter tubing sleeve and joined together using cyclohexanone. In some instances, approximately $10^6$ spores were placed inside of each cut tubing half at the location of the clamps (refer to FIG. 6) prior to tubing reconnection. The tubing was then allowed to remain in the fixture of a minimum of twenty-four hours (in the actual manufacturing process the units will be sterilized immediately after the connection is made) after which the fixture and tubing were exposed to varying doses of irradiation from a 0.6 MeV electron beam accelerator. A Farady cup was used to measure the dose delivered to the outside of the tubing and film dosimeters (FWT) were used to quantify doses at various locations within the tubing. Following irradiation, the inoculated tubings were aseptically removed from the pouches and the inoculated areas individually transferred to 10 ml of sterile water. After sonification for ten minutes, serial dilutions were made and samples were cultured at 30–35 C on tryptic soy agar plates. Inoculated but non-irradiated tubings were used as positive controls.

Results are shown in Table 1. Completed bacterial inactivation was seen at the distal (clamp region) tubing inoculation sites following 2.2 Mrads of radiant energy, however, this dose was insufficient to achieve sterilization at the tubing center, due to reduced electron penetration of the double wall thickness tubing (sleeve) at the site of connection. These studies thus indicated that a higher energy electron beam would be required for effective sterilization.

A second series of studies was performed to evaluate different beam energies/doses. A Pulserad 122A linear electron beam accelerator rated at 1.8 MeV was used for these studies; energy levels of 1.1, 0.9 and 0.75 MeV were evaluated.

To study the variation of beam intensity at various locations within the isolation fixture, dosimeters were placed at the following locations: center of beam, 1½ inches above center, 1½ inches beneath center, within the single walled tubing and within the double walled "sleeve" area of the connection. Approximately 0.5 Mrad was delivered to the tubing contained within the fixture in each of two separate experiments. As shown in Table 2, approximately one-half of the dose delivered to the outside center of the tube was available at the interior of the double walled connection area (=0.31 Mrad). About a 50% falloff in dose also occurred from the beam center to beam periphery. The delivered radiation dose of the beam is gaussian with intensity at the periphery being approximately 50% of the intensity at the center. Since a higher dose is required in the center double wall (sleeve) area due to material thickness, the observed pattern of energy delivery seemed well suited for the application.

Additional studies were performed using *B. Pumilus* pores as a biological indicator. For each dose study, three tubings were placed in the isolation fixture and positioned as would be the case during apheresis kit manufacture. Two tubings were used for inoculation studies while dosimeters were placed within the double-walled central tubing area (junction site) and within the tubing lumen at the clamp occlusion site of the third. A dosimeter was also placed in a paper envelope and attached to a Faraday cup.

Approximately $6.2 \times 10^5$ *B. pumilus* spores were placed at the intended site of reconnection under the double-wall portion of tubing. An additional $8-9 \times 10^5$ *B. pumilus* spores were placed within the interior of each tubing at the points at which it was clamped. After the connection had been made, the tubings and fixture were irradiated using a beam energy of 1.1 MeV. Additional studies were performed using different tubings, inocula and dosimeters; the delivered (exterior) dose in these studies ranged from 0.45 to 6.00 Mrads.

Table 3 shows that while viable biological indicator organisms were recovered when the tubings were exposed to a low dose at an energy of 1.1 MeV irradiation (external dose =0.45 and 1.05 Mrads, respectively), no organisms were recovered from the inoculated sites following external doses of 2.38 Mrads or more. Culture of non-irradiated control samples showed recoveries of from 6 to $9\times10^5$ viable organisms. Table 3 shows bacterial recovery following various doses of electron beam irradiation. Since the D value for *B. pumilus* is 0.15 Mrad, a total dose of 0.15×6= 0.9 Mrad would be anticipated to be needed for a 6-log reduction of viable organisms. The third incremental dose delivered (1.35 Mrads inside the double wall connection area) exceeded the anticipated (0.9 Mrads) dose required for 6-log organism reduction. Thus, with an external dose of 2.38 Mrads and a delivered (worst case) internal dose of 1.35 Mrads, a spore log reduction of 9 was seen within the fluid-contact pathway. Based on anticipated product and manufacturing facility bioburden data, a sterility assurance level of in excess of $10^{-16}$ may be anticipated.

Additional dose/biological indicator studies using 0.9 MeV and 0.75 MeV beam energies were also conducted in a similar manner. At both beam energies, no viable organisms remained following delivery of 2.5 or more megarads of energy (Table 4).

While the above demonstrates the effectiveness of beam energies as low as 0.75 MeV with 2.5 or more megarads of delivered energy, preferably a 2.0 MeV linear electron beam acceleration will be used in actual production.

Calculations also demonstrated that a 10 mm thick aluminum sheet would be expected to be adequate to shield products from 4.5 MeV electrons. This shield thickness is expected to be adequate at both 2.5 and 5.0 Mrad doses.

Subsequently, specific dosimetry and biological indicator studies were performed to quantify the radiation dose delivered to portions of the apheresis kit and solutions external to the isolation fixture/tubing target area. In these studies, dosimeters and *B. pumilus* biological indicator strips were placed on the solution containers. The connected tubing region and the shielded isolation fixture were then subjected to 2.5 Mrad or 5.0 Mrad doses of electron beam irradiation as would take place during the manufacturing technique. No radiation was found to be delivered to the solution containers at either dose of incident radiation (lower limit of dosimeter detection=0.05 Mrad). No significant differences were seen in organism recovery between non-irradiated and shielded/irradiated biological indicator strips, further indicating the adequacy of solution fixture shielding using 10 mm aluminum.

Based upon the above, solution stability/dating is unlikely to be adversely affected by this change in the apheresis kit manufacturing process. Assay of non-irradiated control and shielded/irradiated solutions exposed to 2.5 and 5.0 Mrad doses of radiation did not show significant changes in solution constituents as shown in Table 5.

Apparatus for carrying out the present invention is depicted in FIGS. 8 through 11. FIG. 8 shows an electron sterilization unit having a radiation source 40, radiation shielded housing 42 and a conveyor 44 for loading and unloading the fixture 36 within the radiation shielded housing 42. As depicted there, the fixture 36 is mounted atop a carrier 46 adapted to move along the top of the roller conveyor 44. The product 10, which comprises the medical liquid containers 12 and liquid administration or processing apparatus 14 lies atop the carrier. The tubings 20a–c and 28a–c are fixed in the isolation fixture 36 in the position indicated in FIG. 6.

After the carrier 46 enters the housing 42, it is raised by a piston cylinder arrangement 48 into the position indicated in dashed lines in FIG. 8. The walls of the isolation fixture 36 surround the electron beam emitter and isolate the remaining portions of the product, particularly the medical liquid containers 12, from the radiation resulting from the electron beam. After the carrier is raised to the position shown in dashed lines, the electron beam is turned on to provide the appropriate radiation dose, as discussed in detail above and shown in the preceding tables, to assure sterility of the tubing area between the isolating clamps. Following sterilization, the carrier is lowered and removed from the housing along the roller conveyor 44.

FIG. 9 depicts an alternative embodiment of apparatus which may be used for carrying out the present invention, which does not require as much shielding as the apparatus of FIG. 8, and is believed to be more efficient in its operation. The apparatus depicted in FIG. 9 includes a shielded housing 50, a conveyor 52 upon which product carrier plates 54 move and a shielded closure member 56 mounted for vertical movement by an air or hydraulic cylinder 58.

The detailed construction of the product carrier plate is best seen in FIGS. 10 and 11. The carrier plate has a generally rectangular, flat surface 58 upon which the medical liquid containers 12 and the liquid administration apparatus 14 rest. The tubings 20a–c and 28a–c lie along an outwardly extending and arcuate arm 60 with the flexible plastic sleeves 30 disposed at the end of the arm over a U-shaped aperture.

After the product is placed upon the carrier and the tubing arranged in the manner depicted in FIGS. 10 and 11, the carrier is moved into the position shown in FIG. 9 relative to the shielded housing. The lower closure member 56 is then moved upwardly, nesting tightly against and on the underside of the arm 60. As can be seen from FIG. 9, the end portion of the arm, where the joining flexible plastic sleeves 30 are located is positioned at a lower aperture 62 of the shielded housing which is the focus of the electron beam. The beam is then energized, as described above, to effect sterilization of the isolated portion of the tubings 20a–c and 28a–c. The closure member 56 is then lowered and the carrier removed from the housing along the conveyor 52. The next carrier is then moved into place and these steps are repeated.

The apparatus disclosed in FIGS. 9 through 11 requires less shielding than that depicted in FIG. 8 due, in part, to the arcuate arm 60 (best seen in FIG. 11). The arcuate nature of the arm 60 creates a non-linear serpentine path which greatly restricts the emission of any radiation from the isolated tubing area.

Although the present invention has been described in terms of the preferred embodiment and utilizing a specific product as an example of how it may be employed, the present invention is not limited to the particular product depicted in FIG. 1 or to the apparatus shown in the other drawings. The scope of the present invention is defined by the appended claims.

TABLE 1

| CENTER (DOUBLE THICKNESS [REJOINED] AREA) | | | | | |
|---|---|---|---|---|---|
| SURFACE DOSE (FILM) | FARADAY CUP | TYPICAL INTERIOR OF TUBING DOSE | ORGANISMS REMAINING | END (CLAMP LOCATION) ORGANISMS REMAINING* | |
| | | | | END A | END B |
| 1.00 Mrad | .55 Mrad | .15 Mrad | $3 \times 10^3$ | $1 \times 10^3$ | $4 \times 10^3$ |
| 1.50 Mrad | 1.10 Mrad | .25 Mrad | $2 \times 10^3$ | $9 \times 10^1$ | $4 \times 10^4$ |
| 2.20 Mrad | 2.20 Mrad | .55 Mrad | $1 \times 10^4$ | $4 \times 10^2$ | 0 |
| >2.20 Mrad | 3.30 Mrad | .80 Mrad | $3 \times 10^1$ | 0 | 0 |

*= $4 \times 10^5$ Bacillus pumilus spores recovered from non-irradiated control areas.

TABLE 2

| | DELIVERED DOSE (Mrad) | |
|---|---|---|
| DOSIMETER POSITION | STUDY A | STUDY B |
| Outside Center | .55 | .50 |
| Outside Top | .31 | .31 |
| Outside Bottom | .31 | .31 |
| Within Double Wall | .31 | .22* |
| Within Single Wall | — | .27* |

*Tubing center was ½ inch off beam center.

TABLE 3

| DOSE (Mrad) | | BIOLOGICAL INDICATOR COUNT* | | | | | | SPORE LOG REDUCTION | |
|---|---|---|---|---|---|---|---|---|---|
| OUTSIDE TUBE | INSIDE DOUBLE WALL | TUBING 1 | | | TUBING 2 | | | | |
| | | CENTER | CLAMP A | CLAMP B | CENTER | CLAMP A | CLAMP B | EXPECTED | ACTUAL |
| 0.45 | .23 | $9.0 \times 10^3$ | $3.0 \times 10^4$ | $1.0 \times 10^4$ | $2.0 \times 10^3$ | $3.0 \times 10^3$ | $2.0 \times 10^4$ | 1.50 | 2.00 (1.5–2.6) |
| 1.05 | .575 | $1.5 \times 10^1$ | $4.0 \times 10^2$ | $6.0 \times 10^1$ | $2.0 \times 10^1$ | $6.0 \times 10^2$ | $8.0 \times 10^2$ | 3.80 | 3.80 (3.0–4.6) |
| 2.38 | 1.35 | 0 | 0 | 0 | 0 | 0 | 0 | 9.00 | — |
| 3.05 | 1.60 | 0 | 0 | 0 | 0 | 0 | 0 | 11.00 | — |
| 3.50 | 1.75 | 0 | 0 | 0 | 0 | 0 | 0 | 12.00 | — |
| 4.43 | 2.43 | 0 | 0 | 0 | 0 | 0 | 0 | 16.00 | — |
| 4.80 | 2.50 | 0 | 0 | 0 | 0 | 0 | 0 | 17.00 | — |
| 6.00 | 3.50 | 0 | 0 | 0 | 0 | 0 | 0 | 23.00 | — |

*Controls: Center: $6.2 \times 10^5$ Clamp A: $9.2 \times 10^5$ Clamp B: $8.0 \times 10^5$

TABLE 4

| DOSE (Mrad) | | | BIOLOGICAL INDICATOR COUNT | | % OUTSIDE DOSE PRESENT INSIDE DOUBLE WALL TUBING |
|---|---|---|---|---|---|
| Outside Tubing | Inside Double Wall | Inside Single Wall | TUBING 1 Center | TUBING 2 Center | |
| BEAM ENERGY: 0.9 MeV | | | | | |
| 1.30 | 1.05 | 1.20 | $1.5 \times 10^4$ | $6 \times 10^1$ | 81% |
| 2.50 | 2.03 | 2.30 | 0 | 0 | 81% |
| 3.48 | 2.77 | 3.18 | 0 | 0 | 80% |
| BEAM ENERGY: 0.75 NeV | | | | | |
| 0.90 | .65 | .875 | $3 \times 10^2$ | 8 | 72% |
| 2.65 | 1.85 | — | 0 | 0 | 70% |
| 4.85 | 2.83 | 4.28 | 0 | 0 | 58% |

TABLE 5

Changes in Solution Constituents Following Shielded Exposure to 2.5 and 5.0 Mrads of Electron Beam Radiation

| PRODUCT | TEST | CONTROL | 2.5 Mrad | 5.0 Mrad |
|---|---|---|---|---|
| 0.9% NaCl | pH (Unbuffered) | 6.00 | 4.80 | 4.40 |
| | Chloride (g/L) | 9.05 ± 0.2 | 9.13 ± 0.2 | 9.06 ± 0.2 |
| | Sodium (ID) | POS | POS | POS |
| ACD | Sodium Citrate (g/L) | 22.2 ± 0 | 22.2 ± 0.3 | 22.1 ± 0.3 |
| | Citric Acid (g/L) | 7.32 ± 0.1 | 7.32 ± 0.1 | 7.31 ± 0.1 |
| | Dextrose (%) | 2.47 | 2.47 | 2.49 |
| | pH | 4.90 | 4.90 | 4.90 |
| | Chloride | NMT 20 PPM | NMT 20 PPM | NMT 20 PPM |

What is claimed is:

1. A method for sterilizing a first part of a product portion, said first part having means defining a flow path, said flow path having a proximal end communicating with the remainder of said product portion and a terminal end distal from said proximal end, said method comprising the steps of:

blocking said flow path to the ingress of microorganisms at a location spaced from said terminal end so as to form an isolated terminal end portion;

exposing at least a portion of the interior of said isolated terminal end portion to an non-sterile environment;

exposing at least said isolated terminal end portion to an electron beam while shielding at least a part of the remainder of said product portion from the electron beam; and unblocking said isolated terminal end portion to provide an open flow path between the remainder of said product portion and said terminal end of said flow path.

2. The method of claim 1 said method including the step of exposing said product portion to a selected form of sterilization that does not include electron beam radiation.

3. The method of claim 2 wherein said flow path is blocked after said product portion is sterilized by said selected form of sterilization and before said at least a portion of said interior of said isolated terminal end portion is exposed to a non-sterile environment.

4. The method of claim 1 wherein said product portion includes a plastic container with contents therein and said means defining the flow path comprises a plastic tube and means providing a sterile protector over said terminal end, said method including:

exposing said product portion to a form of sterilization that does not include electron beam radiation;

removing said sterile protector, thereby exposing said at least a portion of said interior of said isolated terminal end portion to a non-sterile environment before the step of exposing at least said isolated terminal end portion to an electron beam.

5. The method of claim 1 wherein said flow path is blocked by providing a frangible closure device disposed within said flow path.

6. A method for sterilizing a first part of a product portion, said first part having means defining a flow path, said flow path having a proximal end communicating with the remainder of said product portion and a terminal end distal from said proximal end, said method comprising the steps of:

isolating the terminal end from the remainder of said product portion by applying a clamp to said flow path at a location spaced from said terminal end so as to form an isolated terminal end portion;

exposing said isolated terminal end portion to a non-sterile environment;

exposing at least said isolated terminal end portion to an electron beam while shielding at least a part of the remainder of said product portion from the electron beam;

opening said isolated terminal end portion to provide an open flow path between the remainder of said product portion and said terminal end of said product portion.

* * * * *